(12) United States Patent
Kantor et al.

(10) Patent No.: US 11,426,110 B2
(45) Date of Patent: Aug. 30, 2022

(54) PRE-CONNECTABLE MEDICAL PATCH ENVELOPE

(71) Applicant: INOVYTEC MEDICAL SOLUTIONS LTD., Hod Hasharon (IL)

(72) Inventors: Ehud Kantor, Hod Hasharon (IL); Nir Barkai, Kfar Sava (IL)

(73) Assignee: INOVYTEC MEDICAL SOLUTIONS LTD., Hod Hasharon (IL)

( * ) Notice: Subject to any disclaimer, the term of this patent is extended or adjusted under 35 U.S.C. 154(b) by 456 days.

(21) Appl. No.: 16/072,954

(22) PCT Filed: Feb. 14, 2017

(86) PCT No.: PCT/IL2017/050188
§ 371 (c)(1),
(2) Date: Jul. 26, 2018

(87) PCT Pub. No.: WO2017/141238
PCT Pub. Date: Aug. 24, 2017

(65) Prior Publication Data
US 2019/0008409 A1 Jan. 10, 2019

Related U.S. Application Data

(60) Provisional application No. 62/295,637, filed on Feb. 16, 2016.

(51) Int. Cl.
*A61B 5/282* (2021.01)
*A61K 9/70* (2006.01)
(Continued)

(52) U.S. Cl.
CPC ............. *A61B 5/282* (2021.01); *A61B 5/259* (2021.01); *A61B 5/274* (2021.01); *A61B 5/6833* (2013.01);
(Continued)

(58) Field of Classification Search
CPC ........... A61B 5/25; A61B 5/251; A61B 5/257; A61B 5/259; A61B 5/28; A61B 5/279;
(Continued)

(56) References Cited

U.S. PATENT DOCUMENTS 4,917,929 A 4/1990 Heinecke
5,254,109 A * 10/1993 Smith .................. A61K 9/7007
600/556

(Continued)

FOREIGN PATENT DOCUMENTS

JP 2000507116 A 6/2000
JP 2005522284 A 7/2005
(Continued)

OTHER PUBLICATIONS

International Search Report for PCT/IL2017/050188, dated May 18, 2017, 4 pages.
(Continued)

*Primary Examiner* — Eun Hwa Kim
(74) *Attorney, Agent, or Firm* — Roach, Brown, McCarthy & Gruber, P.C.; Kevin D. McCarthy (57) ABSTRACT

An envelope is comprised of two sheets of material that are placed one on top of each other with their interior sides facing each other with their edges sealed to each other with an adhesive to form an airtight enclosure. The envelope has at least one medical patch inside it that is attached to the interior side of at least one of the sheets and a layer of medical grade pressure sensitive adhesive surrounding the at least one medical patch. The pressure sensitive adhesive is applied to a part of the surface of the interior side of the sheet in order to attach the sheet of material and the at least one medical patch to the body of a patient. The medical patch can be an electrode for measuring a patient's vital signs or
(Continued)

delivering an electric shock or a transdermal patch for delivering a drug to a patient.

16 Claims, 6 Drawing Sheets

(51) Int. Cl.
  *A61N 1/04* (2006.01)
  *A61B 5/00* (2006.01)
  *A61K 9/00* (2006.01)
  *A61B 5/259* (2021.01)
  *A61B 5/274* (2021.01)

(52) U.S. Cl.
  CPC ............ *A61K 9/0009* (2013.01); *A61K 9/703* (2013.01); *A61N 1/046* (2013.01); *A61N 1/0456* (2013.01); *A61N 1/0492* (2013.01); *A61B 2505/01* (2013.01); *A61B 2562/04* (2013.01); *A61B 2562/125* (2013.01); *A61B 2562/164* (2013.01); *A61B 2562/242* (2013.01); *A61K 9/7023* (2013.01)

(58) Field of Classification Search
  CPC ... A61B 5/6804; A61B 5/6805; A61B 5/6823; A61B 5/6833; A61B 5/68335; A61B 2505/01; A61B 2562/04; A61B 2562/125; A61B 2562/164; A61B 2562/242; A61F 13/00; A61F 2013/00089; A61F 2013/00106; A61F 2013/00289; A61N 1/0456; A61N 1/046; A61N 1/0492; A61K 9/7023
  See application file for complete search history.

(56) References Cited

U.S. PATENT DOCUMENTS

| | | | |
|---|---|---|---|
| 5,827,184 A * | 10/1998 | Netherly | A61N 1/0472 600/372 |
| 5,958,447 A | 9/1999 | Haralambopoulos | |
| 6,135,953 A | 10/2000 | Carim | |
| 6,151,869 A * | 11/2000 | Weder | A01G 5/04 53/219 |
| 6,935,889 B2 * | 8/2005 | Picardo | A61N 1/046 600/392 |
| 7,027,864 B2 | 4/2006 | Snyder et al. | |
| 7,278,424 B1 | 10/2007 | Davies | |
| 7,822,488 B2 * | 10/2010 | Jonsen | A61N 1/0472 607/142 |
| 7,848,824 B2 | 12/2010 | Anderson | |
| 8,170,639 B2 | 5/2012 | Hauge et al. | |
| 9,585,620 B2 * | 3/2017 | Paquet | G16H 40/67 |
| 10,226,615 B2 * | 3/2019 | Lang | A61N 1/0476 |
| 2003/0171798 A1 * | 9/2003 | Nova | A61N 1/04 607/142 |
| 2006/0142831 A1 | 6/2006 | Nova | |
| 2006/0155251 A1 * | 7/2006 | Assie | A61F 13/0203 604/306 |
| 2008/0210592 A1 * | 9/2008 | Anderson | A61N 1/0472 206/701 |
| 2012/0253162 A1 | 10/2012 | Jones | |
| 2016/0279405 A1 * | 9/2016 | Riley | A61N 1/3993 |

FOREIGN PATENT DOCUMENTS

| | | |
|---|---|---|
| JP | 2010508940 A | 3/2010 |
| WO | 2014070123 A1 | 5/2014 |
| WO | 2015/068164 A1 | 5/2015 |

OTHER PUBLICATIONS

Written Opinion of the International Searching Authority for PCT/IL2017/050188, dated May 18, 2017, 6 pages.

Office action from Japanese patent office for counterpart application No. 2018-543363 0 (dated Nov. 20, 2020) 4 pages; and a machine English translation thereof (5 pages).

European Patent Office Communication regarding application No. 17752796.7; dated Jun. 12, 2019; 8 pages.

* cited by examiner

PRE-CONNECTABLE MEDICAL PATCH ENVELOPE

FIELD OF THE INVENTION

The invention is from the field of medical equipment. Specifically the invention relates to medical patches that are applied to the body of a patient. More specifically the invention relates to packaging for storing and applying medical electrodes and transdermal patches that are attached to the bodies of patients for different purposes.

BACKGROUND OF THE INVENTION

One of the common procedures in medical practice is attachment of electrodes to a human body either for monitoring body functions such as in ECG or EEG or for therapy such as defibrillation. Trained medical personnel know how to quickly apply these electrodes to the proper location when necessary but doing so can be quite a challenge for untrained persons, who sometimes find themselves in a situation where they are called upon to administer medical aid.

Medical emergency situations may occur in various circumstances and affect different body functions such as: trauma injuries, central nerve system injuries (e.g. stroke with apnea), cardiac conditions (e.g. coronary artery disease or cardiac arrhythmias) respiratory conditions (e.g. pulmonary embolism and chronic obstructive lung disorder, or pulmonary spastic disease), there are also systemic conditions such as anaphylactic shock, that affect multiple body functions.

Immediate medical assistance is critical to the effectiveness of life saving treatment in emergency cases. More often than not, professional medical personnel are not present at the scene of occurrence of an emergency situation, leaving the conduct of first emergency care to a lay person bystander, who is any person physically present at the scene at the time of emergency occurrence, who is capable and willing to assist, despite the lack of professional medical qualifications. The layperson care giver is therefore dependent upon lifesaving equipment which must be ultra-user friendly, as it assumes little or no medical knowledge whatsoever of the layperson care giver.

One type of critical care device that is relatively commonly available in public places is an Automated External Defibrillator (AED) device, which is a portable electronic device that applies electrical shock therapy for the treatment of cardiac arrhythmias. In the simplest of these devices, the caregiver is required to attach two electrodes to the chest of the patient. These are dual purpose electrodes that can measure ECG in one mode of operation and administer electric shock in another.

Depending on the degree of sophistication of the AED some of them require attachment of additional electrodes to measure various vital signs. An example of the latter type of device can be found in WO 2015/068164, which describes a portable system for providing decision-assisted critical care to a patient in medical emergency situations in an out of hospital setting. The system comprises components for applying oxygen therapy as well as an AED and a controller, configured to guide a caregiver in using the device.

AED is used with an unconscious patient. One of the challenges in treating a conscious patient with coronary artery disease (CAD) is the deterioration into unconscious, sudden cardiac arrest (SCA) and the need for continuously monitoring the patient's ECG with the use of additional electrodes in order to alert the care-giver and to start the AED process immediately. The time interval from SCA to defibrillation is critical and every minute saved contributes to a better outcome.

The term "transdermal patch" as used herein refers to a medicated adhesive patch that is placed on the skin to deliver a specific dose of medication through the skin and into the bloodstream. An advantage of a transdermal drug delivery route over other types of medication delivery such as oral, topical, intravenous, intramuscular, etc. is that the patch provides a controlled release of the medication into the patient.

It is a purpose of the present invention to provide electrodes and transdermal patches for medical purposes that are packaged in a manner that facilitates their easy and fast application to a human body.

Further purposes and advantages of this invention will appear as the description proceeds.

SUMMARY OF THE INVENTION

Herein the word "patient" is used in its broadest sense to mean a person who receives medical care or treatment for any reason. This includes persons undergoing routine testing or undergoing a medical procedure in a doctor's office, clinic, or hospital as well as persons undergoing emergency treatment as the result of a sudden illness or traumatic injury.

In a first aspect the invention is an envelope comprised of either one sheet of material that is folded along a central fold line with the remaining three edges sealed to each other with an adhesive to form an airtight envelope or of two sheets of material that are placed one on top of each other with their interior sides facing each other with their four edges sealed to each other with an adhesive to form an airtight envelope. The envelope has at least one medical patch inside it that is attached to the interior side of at least one of the sheets and a layer of medical grade pressure sensitive adhesive surrounding the at least one medical patch. The pressure sensitive adhesive is applied to a part of the surface of the interior side of the sheet in order to attach the sheet of material and the at least one medical patch to the body of a patient.

In embodiments of the envelope of the invention, electrical contacts attached to the backs of the at least one medical patch poke through the sheet from the interior side of the sheet to the external side of the sheet.

In embodiments of the envelope of the invention electrical leads are pre-connected to electrical contacts attached to the at least one medical patch during the manufacture stage.

In embodiments of the envelope of the invention the electrical contacts attached to the at least one medical patch do not poke through to the exterior side of the sheets and electrical leads are pre-connected directly to the at least one medical patch and either coiled up and sealed inside the envelope to be uncoiled when the envelope is opened or pass between the edges of the two sheets to the outside with the adhesive used to seal the envelope forming an air tight seal around them.

Embodiments of the envelope of the invention comprise a controller that is pre-connected to electrical leads that are pre-connected to electrical contacts attached to the at least one medical patch. The controller is either enclosed within the envelope or is attached to the exterior of the envelope.

In embodiments of the envelope of the invention sealing of the two sheets of material together is done with a type of adhesive that will create a seal that maintains the integrity of the envelope to insure sterility of the at least one medical patch and freshness of the medical grade adhesive layer and allows easy separation of the two sheets when required without tearing them.

In embodiments of the envelope of the invention instructions for the correct placement of the medical patch are printed on the exterior of the envelope.

In embodiments of the envelope of the invention the at least one medical patch is one of;
a) an electrode for medical purposes or biomedical research; and
b) a transdermal patch for administering medication to a patient.

In embodiments of the envelope of the invention the at least one medical patch is an electrode and the envelope comprises a layer of gel that covers each electrode. In these embodiments sealing of the two sheets of material together is done with a type of adhesive that will create a seal that maintains the integrity of the envelope to insure sterility of the at least one medical patch and freshness of the gel and the medical grade adhesive layer and allows easy separation of the two sheets when required without tearing them.

Embodiments of the envelope of the invention comprise electrodes on both of the sheets of material that make up the envelope and a non-stick liner placed between the two sheets of material.

In embodiments of the envelope of the invention that comprise electrodes on both of the sheets of material the non-stick liner is present only if the areas covered with adhesive around the electrodes overlap each other when the two sheets are assembled to form the envelope.

In embodiments of the envelope of the invention that comprise a liner separating the two sheets of material the liner can be automatically removed when the two sheets of the envelope are separated from each other.

In embodiments of the envelope of the invention envelopes containing the same arrangement of at least two electrodes are supplied in different sizes with different distances between electrodes to insure correct placement of the electrodes.

In a second aspect the invention is a method of applying the at least one medical patch in the envelope of the first aspect of the invention to the skin of a patient. The method comprises: separating the two sheets of material that form the envelope, placing the sheets of material with the interior side facing the patient and the at least one medical patch at the designated location on the body of the patient, and pressing on the exterior side of the sheets of material to cause the sheet and the at least one medical patch to adhere to the skin of the patient.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

In a first embodiment the medical patch is an electrode and the invention is an envelope comprising electrodes for application to the body of a patient. The electrodes, together with gel and adhesive are pre-sealed and ready to use within the envelope. The purpose of the envelope of the invention is to store medical electrodes designed for one time use in a manner that maximizes the length of time for which they can be stored and mainly to provide a simple and speedy method of application of the electrodes to a patient in time of need.

Embodiments of the envelopes of the invention can comprise any type of electrode for medical purposes, such as: EEG, ECG, ECT, defibrillation, and electrodes for electrophysiology techniques in biomedical research.

The envelopes can contain one or more electrodes depending upon the application, for example, two electrodes for defibrillation or one, three, or twelve electrodes for one, three, or twelve lead ECG respectively.

The envelope of the invention is comprised of two thin sheets of material such as paper, plastic, and paper laminated with a layer of plastic. The backs of the electrodes are attached to one side (herein the interior side) of one or both of the sheets. In an embodiment the electrical contacts to the electrodes poke through the sheet to its exterior side. Depending on the intended use, single electrodes or arrays comprising two or more electrodes can be attached to one or both of the sheets that make up the envelope.

After the electrodes are attached to the two sheets, gel is spread to cover the area over and surrounding the electrodes and a layer of medical grade pressure sensitive adhesive of a type known in the art for attaching the sheets with attached electrodes directly to the body of the patient is applied to the surface of the interior side of the sheets surrounding the area covered by gel.

If there are electrodes on both of the sheets of material that make up the envelope and if the areas covered with adhesive around the electrodes overlap each other when the two sheets are assembled to form the envelope as described below, then a non-stick liner, for example made from polyethylene film that is coated with silicon on one or both surfaces, is placed between them. In this case the liner further assists in maintaining the gel in close contact with the electrodes.

To assemble the envelope, the two sheets of material are placed one on top of each other with the interior sides facing each other and a liner between them if necessary. The edges of the two sheets are then sealed to each other with a heat or pressure sensitive adhesive to form an airtight envelope that has inside it the electrodes covered with gel and adhesive for attaching the electrodes to the body of a patient. The sealing of the two sheets of material together is done with a type of adhesive that will create a seal that, on the one hand, maintains the integrity of the envelope to insure sterility of the electrodes and freshness of the gel and adhesive layers, and on the other hand, allows easy separation of the sheets when required without tearing them.

In an embodiment of the invention the envelope can be made from one sheet of material with a fold line dividing it into two equal parts. Each part of the sheet is treated as one of the separate sheets described above. After attachment of the medical patch or electrodes and application of the gel and liner if necessary, the sheet of material is folded along the fold line and sealed along the remaining three edges.

Embodiments of the invention will now be described with reference to the figures in order to illustrate the invention. The invention is not limited to the specific embodiments shown and, as mentioned herein above, the envelope can be made of different materials and can contain one or more electrodes. In the figures, circle 10 symbolically represents the electrode covered with gel, circle 12 symbolically represents the gel covered area, circle 14 symbolically represents the area covered by adhesive, and numeral 16 identifies the adhesive used to seal the two sheets of material to form the envelope.

Figure 1A:
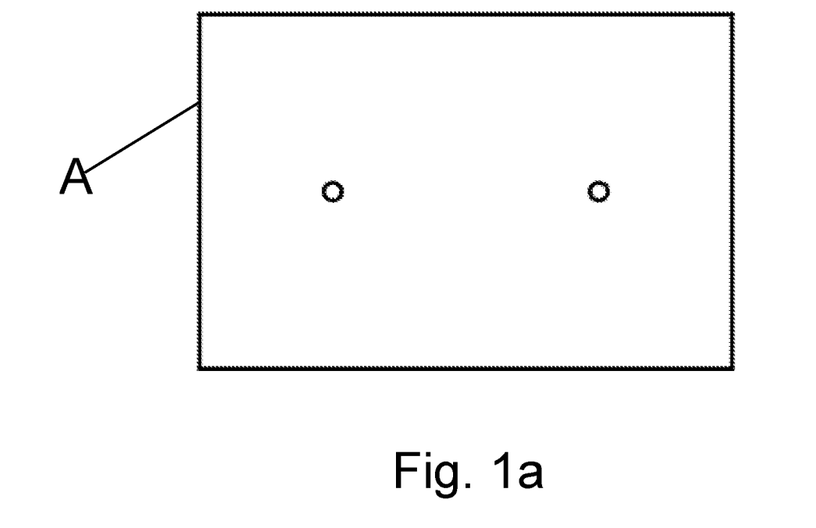
FIG. 1a and FIG. 1b show schematically the electrical contacts on the exterior sides of two pieces of material that will be assembled to form an envelope configured for use with a 3-lead ECG.
Figure 1B:
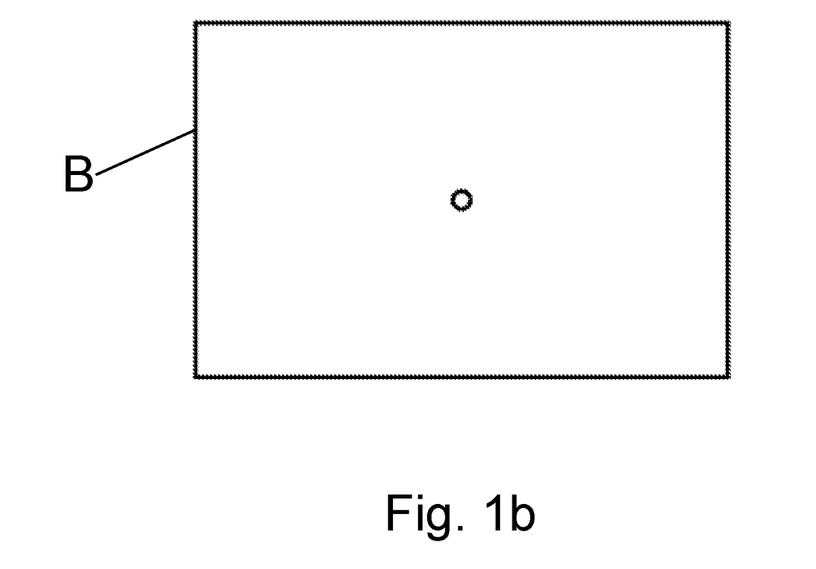

FIG. 1a and FIG. 1b show schematically the electrical contacts on the exterior sides of piece of material A, comprising two electrodes on the interior side, and B, comprising one electrode on its interior side during the manufacture stage. Pieces of material A and B will be assembled to form an envelope configured for use with a 3-lead ECG.

Figure 2A:
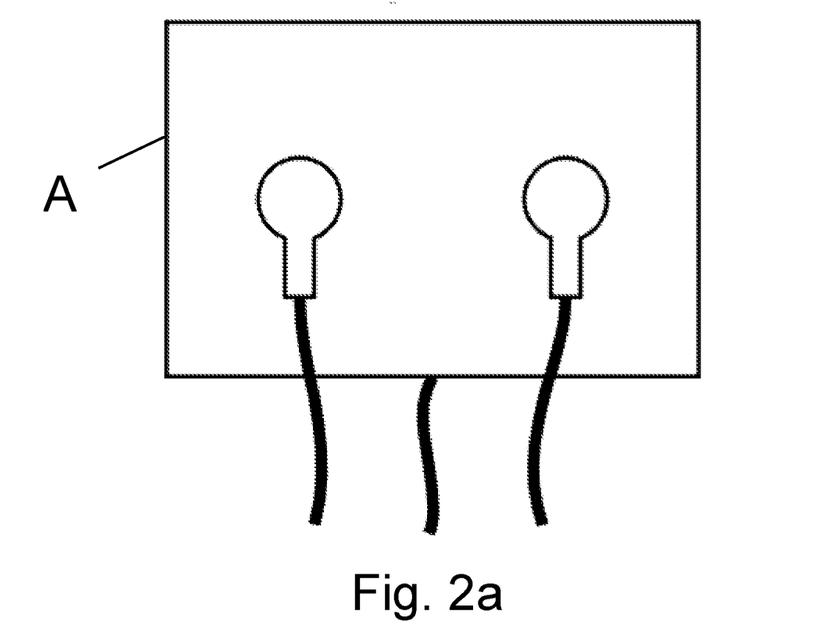
FIG. 2a and FIG. 2b show schematically the two pieces of paper of FIG. 1a and FIG. 1b with electrical leads pre-connected to the electrical contacts.
Figure 2B:
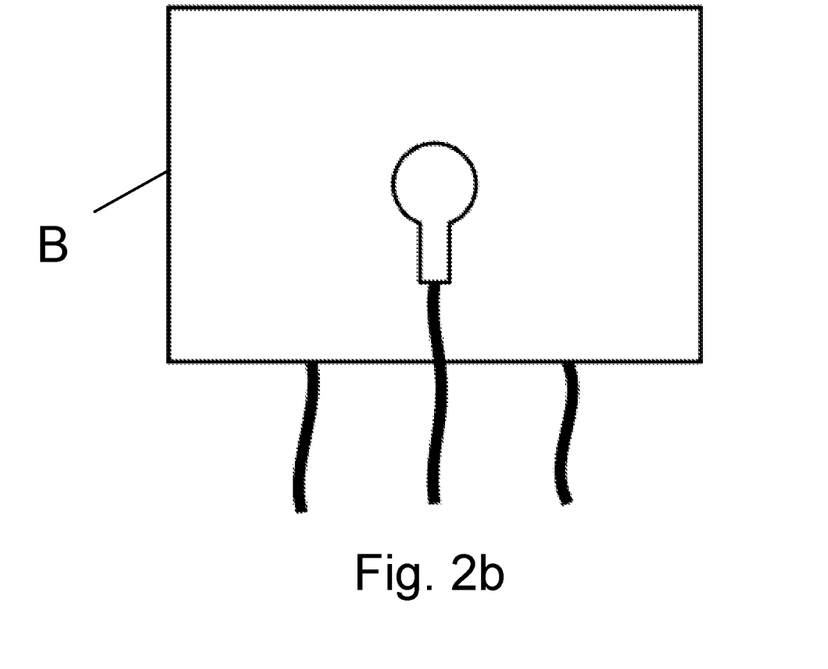

FIG. 2a and FIG. 2b show schematically the two pieces of material of FIG. 1a and FIG. 1b with electrical leads pre-connected to the electrical contacts before use. This is the favored way of supplying the envelope since with this arrangement there is no time taken or possible error in connecting the controller leads to the electrodes and the user simply has to open the envelope and invert and press it onto the body of a patient. In another embodiment the envelope is supplied without the controller electrical leads. In this pre-connectable embodiment the connection is made by a user either before or after applying the electrodes to the body of a user.

In embodiments of the envelope, the electrical contacts of the electrodes do not poke through to the exterior side of the sheets as shown in FIGS. 1a and 1b. In these embodiments the electrical leads are pre-connected directly to the electrodes inside the envelope. The leads can be coiled up and sealed inside the envelope and uncoiled and connected to the external controller when the envelope is opened. Alternatively the wires of the leads can pass between the edges of the two sheets to the outside with the adhesive used to seal the envelope forming an air tight seal around them.

In embodiments of the invention a controller is enclosed within an envelope or is attached to the envelope externally. The controller can be a relatively small and inexpensive device that is pre-connected to the electrode as described herein. Such a controller can be an independent unit or a communication unit that receives instruction from an external device.

Figure 3A:
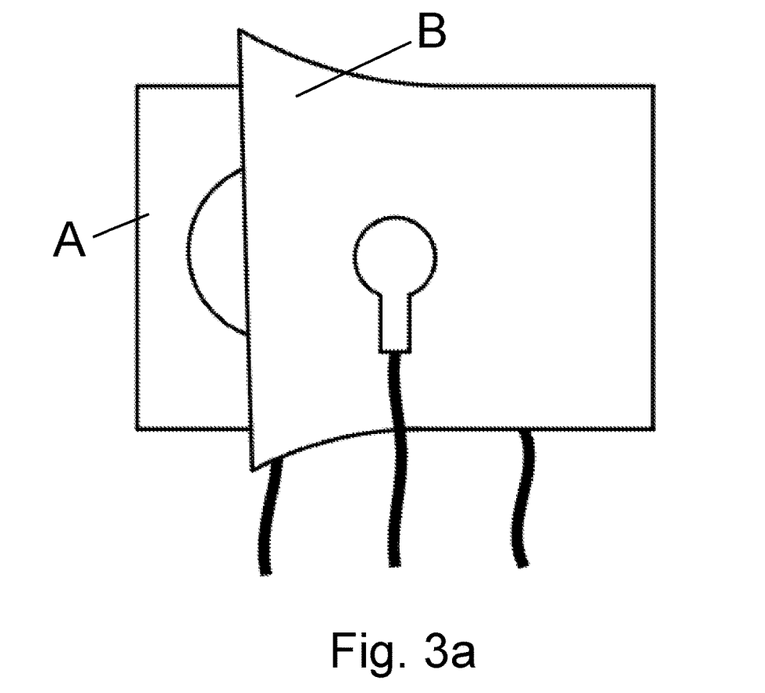
FIG. 3a to FIG. 3b schematically show different stages in the process of opening the envelope to expose the electrodes and FIG. 3c shows the sheets are completely seperated.
Figure 3B:
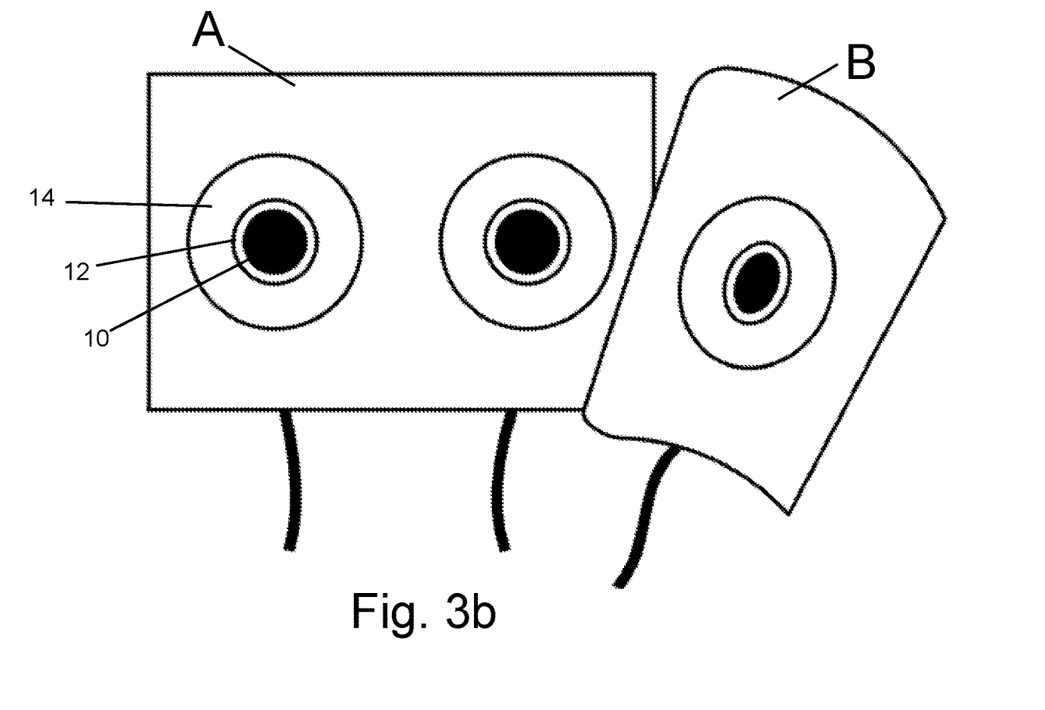
Figure 3C:
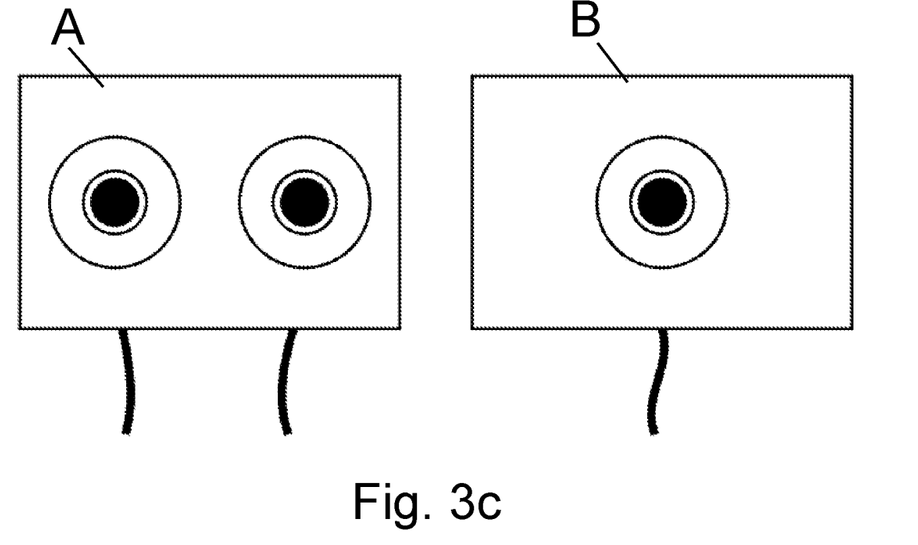

FIG. 3a to FIG. 3b schematically show different stages in the process of opening the envelope to expose the electrodes. In FIG. 3a the sealed edges of sheets A and B on one of the sides of the envelope are separated. In FIG. 3b sheets A and B are pulled apart further separating the sealed edges around the border of the envelope. In FIG. 3c sheets A and B are completely separated. They can now be inverted and pressed onto the body of a patient, where they will be held in position by the adhesive on the sheet.

Figure 4A:
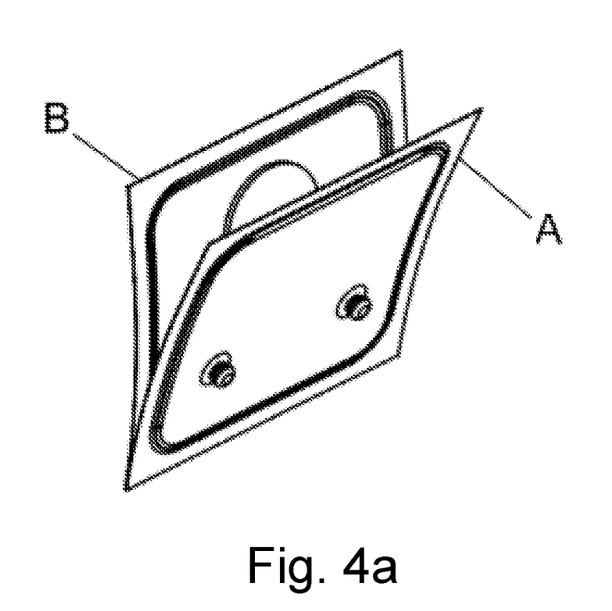
FIGS. 4a to 4c schematically show how the liner separating the two pieces of paper is automatically removed when the two sides of the envelope are separated from each other.
Figure 4B:
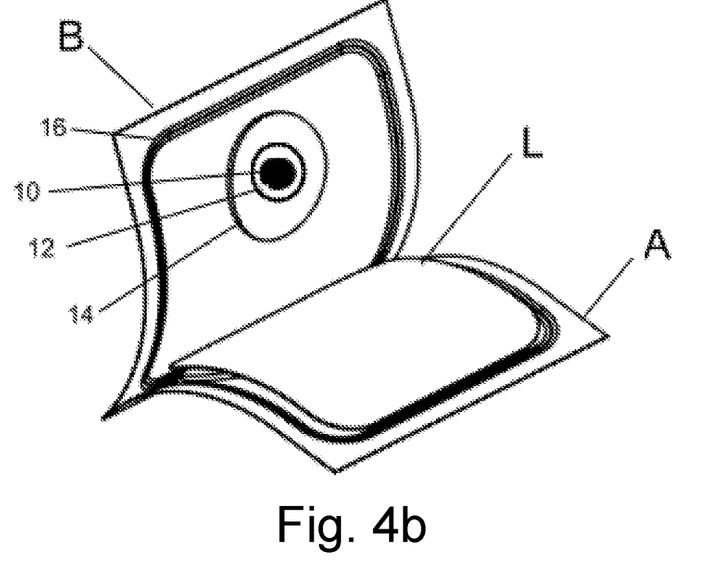
Figure 4C:
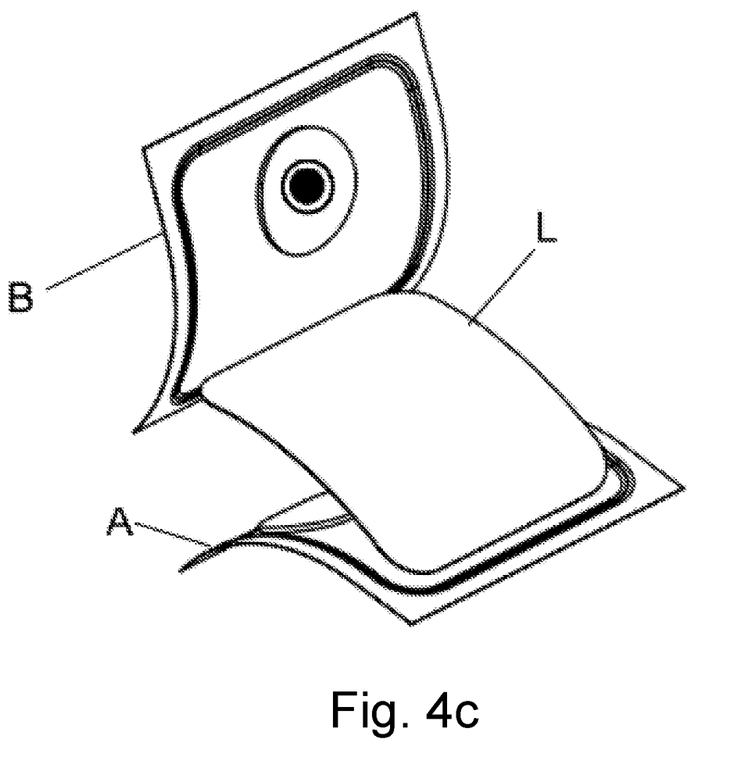

FIGS. 4a to 4c schematically show how the liner separating the two pieces of material is automatically removed when the two sides of the envelope are separated from each other. In FIG. 4a the two pieces of material A and B that comprise the envelope are starting to be pulled apart. In FIG. 4b pieces of material A and B are pulled far enough apart to show liner L between them covering the adhesive covered portions of the interior surfaces. In FIG. 4c pieces of material A and B are pulled further apart. Opposite edges of liner L are attached to each of A and B. Further separation of A and B will cause L to become detached from one or both pieces of material. At this point L has automatically fallen away exposing the electrodes on both sides of the envelope and allowing the pieces of material to be attached to the patient.

Figure 5:
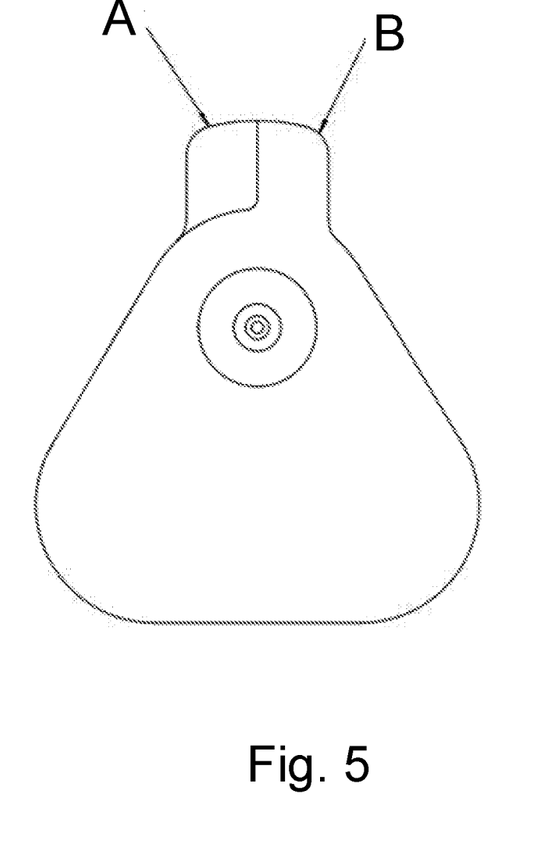
FIG. 5 shows an embodiment of the envelope of the invention.

FIG. 5 shows an embodiment of the envelope of the invention. This embodiment features tabs on pieces of sheet A and B making it even easier and faster to separate them in order to attach the electrodes contained within the envelope to the body of a patient.

In order to apply the electrodes a non-experienced user or a medical professional simply has to separate the two parts of the envelope, to place the sheets of material that form the envelope with their interior sides facing the patient and the electrodes at the designated location on the body of the patient, and to press on the exterior side of the sheet of material to cause the sheet and the electrode to adhere to the skin of the patient.

Note that instructions for the correct placement of the electrodes could be printed on the exterior of the envelope or could be provided to the care-giver in another way; but, in any case, the location of the electrodes is not relevant to the present invention. It is also to be noted that application of the electrodes is simplified by the fact that at least some of them, such as those of sheet A in the figures are already arranged in arrays that have a fixed distance between them. Envelopes containing the same arrangement of electrodes are supplied in different sizes with different distances between electrodes, for example for infants, children, and small, medium or large adults, to insure correct placement of the electrodes.

ECG electrodes are typically supplied in packages of 50-100 electrodes. All electrodes in the package must be either used or discarded within a relatively short period of time, e.g. a month. This results in a considerable amount of waste for facilities that do not use large quantities of these electrodes. Therefore another aspect of the invention is that packaging individual and arrays of electrodes in the envelopes of the invention as described herein above can provide a considerable benefit in preserving the lifetime of the electrodes with attendant financial benefit.

In a second embodiment the medical patch is a transdermal patch and the invention is an envelope comprising a transdermal patch for application to the body of a patient. Non-limiting examples of medications administered by the transdermal patches contemplated by the present invention include small molecules, peptides, nucleic acids, hormones, and vitamins.

The description above of the envelopes of the first embodiment of the invention described applies also to the second embodiment mutatis mutandis with the electrode/s replaced with a transdermal patch.

In one embodiment, the envelope contains a transdermal patch that is integrated to one of the envelope sheets. The patch contains a medication and adhesive for attaching it to the body of a patient sealed within the envelope. Upon opening of the envelope the patch is ready to be applied to the body of the patient with no additional steps required.

In some embodiments control of the release of medication from the patch is performed by current or voltage applied by an electrical circuit. The envelope patch of the present invention is configured to be pre-connected or pre-connectable to a controller comprising a power source and the electrical circuit for managing the controlled release of the medication from the patch.

In some embodiments the controller is connected directly to the exterior of the envelope. The controller may function as an independent unit having the ability to execute the controlled release of the medication. Alternatively, the controller may have a communication function e.g. Wi-Fi, Bluetooth, and cellular. In this configuration the command to release the medication may be communicated to the controller from a remote device such as, but not limited to, a computer or a smartphone.

Although embodiments of the invention have been described by way of illustration, it will be understood that the invention may be carried out with many variations, modifications, and adaptations, without exceeding the scope of the claims.

The invention claimed is:

1. An envelope comprised of either
   a) one sheet of material that is folded into two parts along a fold line with the remaining edges of the two parts sealed to each other with an adhesive to form an airtight envelope or
   b) two sheets of material that are placed one on top of each other with their interior sides facing each other and their edges sealed to each other with an adhesive to form an airtight envelope;
   the envelope containing:
   i) at least one medical patch attached to the interior side of each one of the two parts or two sheets;
   ii) a layer of adhesive applied to a part of the surface of the interior side of the two parts or two sheets surrounding each one of the medical patches;
   the envelope characterized in that:
   A) each medical patch is attached to its respective part or sheet such that each one of the medical patches and the areas covered by the layer of adhesive surrounding each one of the medical patches on the two parts or two sheets do not overlap each other when the two parts or two sheets are assembled to form the envelope; and
   B) when the envelope is opened by pulling apart the sealed edges of the envelope, thereby separating the two parts or two sheets, the layer of adhesive surrounding each one of the medical patches is configured to hold the two parts or two sheets and the attached medical patches to a body of a patient when the interior sides of the two parts or two sheets are pressed onto the body.

2. The envelope of claim 1, wherein electrical contacts attached to the backs of the at least one medical patch poke through the part or the sheet from the interior side of the part or the sheet to the external side of the part or the sheet.

3. The envelope of claim 1, wherein electrical leads are pre-connected to electrical contacts attached to the at least one medical patch during the manufacture stage.

4. The envelope of claim 3, wherein the electrical contacts attached to the at least one medical patch do not poke through to the exterior side of the part or sheet and the electrical leads are pre-connected directly to the at least one medical patch and either coiled up and sealed inside the envelope to be uncoiled when the envelope is opened or pass between the edges of the two parts or two sheets to the outside with the adhesive used to seal the envelope forming an air tight seal around them.

5. The envelope of claim 3 comprising a controller enclosed within the envelope or attached to the exterior of the envelope, the controller pre-connected to the electrical leads that are pre-connected to electrical contacts attached to the at least one medical patch.

6. The envelope of claim 1, wherein sealing of the two parts or two sheets of material together is done with a type of adhesive that will create a seal that maintains the integrity of the envelope to insure sterility of the at least one medical patch and freshness of the medical grade adhesive layer and allows easy separation of the two parts or two sheets when required without tearing them.

7. The envelope of claim 1, wherein instructions for the correct placement of the medical patch are printed on the exterior of the envelope.

8. The envelope of claim 1, wherein the at least two medical patches are selected from:
   a) electrodes for medical purposes or biomedical research; and
   b) transdermal patches for administering medication to a patient, wherein the transdermal patch is configured to be pre-connected or pre-connectable to a controller comprising a power source and electrical circuit for applying current or voltage to manage controlled release of the medication from the transdermal patch.

9. The envelope of claim 8, wherein the medical patch is an electrode and the envelope comprises a layer of gel that covers each electrode.

10. The envelope of claim 8, wherein sealing of the two parts or two sheets of material together is done with a type of adhesive that will create a seal that maintains the integrity of the envelope to insure sterility of the at least one medical patch and freshness of the gel and the medical grade adhesive layer and allows easy separation of the two parts or two sheets when required without tearing them.

11. The envelope of claim 8, comprising electrodes on both of the parts or sheets of material that make up the envelope.

12. The envelope of claim 8, wherein envelopes containing the same arrangement of at least two electrodes are supplied in different sizes with different distances between electrodes to insure correct placement of the electrodes.

13. A method of applying the at least one medical patch in the envelope of claim 1 to the skin of a patient, comprising: separating the two parts or two sheets of material that form the envelope, placing the parts or sheets of material with the interior side facing the patient and the at least one medical patch at the designated location on the body of the patient, and pressing on the exterior side of the parts or sheets of material to cause the part or sheet and the at least one medical patch to adhere to the skin of the patient.

14. The envelope of claim 1, comprising a non-stick liner between the two parts or two sheets when the two parts or two sheets are assembled to form the envelope.

15. The envelope of claim 14, wherein the liner separating the two parts or two sheets of material is automatically removed when the envelope is opened by separating the two parts or two sheets from each other.

16. The envelope of claim 1 wherein the adhesive surrounding each one of the at least one medical patches on each of the two parts or two sheets of the envelope is a medical grade pressure sensitive adhesive.

* * * * *